United States Patent [19]

Kurtz et al.

[11] Patent Number: 4,955,877

[45] Date of Patent: Sep. 11, 1990

[54] AUTOTRANSFUSION BAG

[75] Inventors: Robert J. Kurtz, New York; Joseph LiCausi, Port Jefferson Station, both of N.Y.

[73] Assignee: BioResearch, Inc., Farmingdale, N.Y.

[21] Appl. No.: 418,151

[22] Filed: Oct. 6, 1989

[51] Int. Cl.$^5$ .............................................. A61M 5/00
[52] U.S. Cl. ..................................... 604/408; 604/319
[58] Field of Search ............... 604/407, 408, 409, 319, 604/320, 321, 322, 4; 383/43, 119; 222/105, 183

[56] References Cited

U.S. PATENT DOCUMENTS

| | | | |
|---|---|---|---|
| 3,845,765 | 11/1974 | Ikeda | 604/319 |
| 4,429,693 | 2/1984 | Blake et al. | 604/319 X |
| 4,443,220 | 4/1984 | Hauer et al. | 604/408 |
| 4,573,992 | 3/1986 | Marx | 604/408 |
| 4,642,088 | 2/1987 | Günter | 604/319 X |
| 4,675,010 | 6/1987 | Siposs et al. | 604/319 |
| 4,775,360 | 10/1988 | Lane et al. | 604/319 X |
| 4,838,872 | 6/1989 | Sherlock | 604/319 |

*Primary Examiner*—Robert A. Hafer
*Assistant Examiner*—Lynda M. Cofsky
*Attorney, Agent, or Firm*—Larson and Taylor

[57] ABSTRACT

An autotransfusion bag is provided with semi-rigid side walls and flexible material interconnecting the side walls. The bag is provided with spreader arms which extend across the top of the bag and across the bottom of the bag engaging retainer elements mounted on the external face of the side walls. The spreader arms maintain the bag in an open position to permit the bag to be filled with blood. When the bag is filled, the spreader arms may be removed to permit the bag to collapse as the blood is being reinfused to the patient.

4 Claims, 2 Drawing Sheets

AUTOTRANSFUSION BAG

The present invention relates to autotransfusion bags and more particularly to a bag having spreader arms to maintain the bag in open position while the bag is being filled wherein after the bag is filled the spreader arms are readily removable to permit the bag to be collapsed as the bag is being emptied.

BACKGROUND OF THE INVENTION

During surgical procedures it is desirable to provide means for collecting the patient's blood from the surgical site, collecting the blood in a bag and reinfusing the patient with his own blood upon completion of the operation. There have been numerous developments recently in the field of autotransfusion devices wherein bags are provided with an inlet tube to draw the blood from the surgical site and deposit it within the bag together with suction means for creating suction within the bag to draw the blood from the surgical site into the bag. In order to provide suction within the bag, it is necessary that the bag be maintained in an open position. However, when the blood in the filled bag is to be reinfused into the patient, it is necessary that the bag be collapsible so as to prevent air from entering the bag.

There have been a number of patents directed to providing autotransfusion bags having means for maintaining the bag in an open position and permitting the bag to collapse when the blood within the bag is to be reinfused into the patient. The Hauer U.S. Pat. No. 4,443,220 provides a flexible bag which is maintained in an open position by means of an external supporting frame which engages pockets on the external face of the bag. When the bag is to be emptied, it is simply removed from the frame so as to permit the bag to collapse.

The Sherlock U.S. Pat. No. 4,838,872 also discloses an autotransfusion device including semi-rigid side walls which are flexibly interconnected including a rigid external cylinder which retains the side edges of the semi-rigid side walls of the bag in a compressed position so as to force the side walls outwardly to a substantially cylindrical shape. Thus, the bag is held in an open position by an external rigid cylinder and when the bag is to be emptied, the external cylinder is removed to permit the bag to collapse.

A further type of reinfusion apparatus is shown in the Gunter U.S. Pat. No. 4,642,088 in which an accordion-like bag structure is provided which is held in an expanded condition by means of spring members attached to the end walls which draw the accordion-like bag structure outwardly.

While devices such as discussed hereinbefore have been effective in maintaining an autotransfusion bag in an expanded position while blood is being drawn into the bag and permitting the bag to collapse when blood is to be withdrawn from the bag, such prior devices are relatively complex and expensive to manufacture. The present invention provides a simplified structure which meets all of the requirements of an autotransfusion device with relatively few inexpensive parts.

SUMMARY OF THE INVENTION

The present invention provides a bag for use as an autotransfusion apparatus which comprises semi-rigid side walls interconnected on the side edges and ends by a flexible wall structure. A blood inlet port, suction port and blood outlet port are provided in the end walls of the bag. Rigid spreader arms engage sockets which are mounted on the external surfaces of the semi-rigid side walls of the bag. When the tips of the spreader arms engage in the sockets on the side walls, the bag is maintained in an open extended position. When the filling operation of the bag is completed, the spreader arms may be readily removed from the sockets on the bag side walls, thus permitting the bag to collapse as blood is withdrawn from the bag.

An object of the present invention is to provide an autotransfusion device which provides a reliable inexpensive means for maintaining an autotransfusion bag in open position.

Another object of the present invention is to provide a flexible autotransfusion bag having semi-rigid side walls which are provided with external sockets to engage a spreader arm extending across an end wall of the bag to maintain the bag in an open position during filling operations.

Other objects of the present invention will become more readily apparent upon consideration of the following detailed specification in connection with the accompanying drawings wherein:

DETAILED DESCRIPTION OF THE PREFERRED EMBODIMENT

Figures 1, 2:
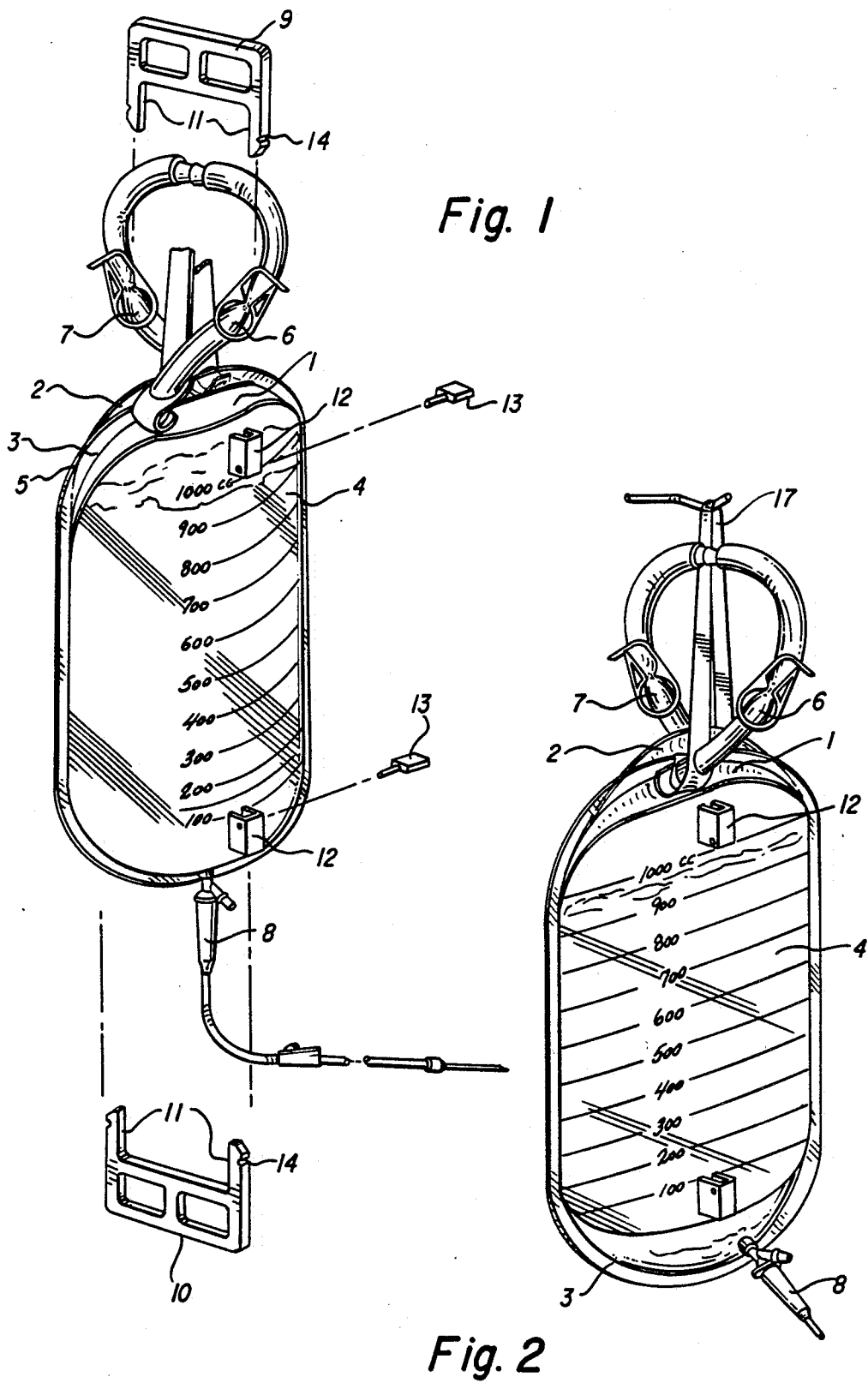
FIG. 1 is a perspective view of an autotransfusion bag in open position showing the spreader arms and locking means in exploded form.
FIG. 2 is a view of the bag in collapsed condition.

There is shown at FIG. 1 an autotransfusion bag according to the present invention. While the autotransfusion bag may be made of different materials and assembled in various ways, in one specific embodiment of the invention there is provided an inner bag having laminated thereto a pair of outer sidewall shells made of semi-rigid plastic. The inner bag comprises a pair of sheets 1 and 2 which may be polyvinyl chloride film having semicircular end portions with the edges of the sheets being heat bonded together as shown at 3. The outer sidewall semi-rigid shells 4 and 5 may, for example, be made of polyethylene terephthalate sheet material of approximately 0.094 inch thickness. The sidewall shells 4 and 5 have semicircular ends and are of a length substantially less than the length of the sheets 1 and 2 of the inner bag. For example, in the embodiment shown, the sheets 1 and 2 may have a length of 12.15" and a width of 6.50" while the sidewall shells 4 and 5 have a length of 8.75" and a width of 6". Thus, when the inner sheets 1 and 2 are bonded together around the edges with a 0.25 seam and the sidewall shells 4 and 5 are centrally bonded to the sheets 1 and 2 the seam of 0.25" extends along each side edge of the sidewalls of the bag and the sheets 1 and 2 extend beyond the ends of the sidewall shells at each end by 1.45" plus the width of the seam of 0.25". When the sidewall shells are forced apart to an outwardly curved shape the portions of the sheets 1 and 2 of the inner bag which extend beyond the ends of the sidewall shells form the top and bottom walls of the expanded inner bag.

The upper end wall of the bag is provided with an inlet port and tube 6 to receive blood from the surgical site. The upper end wall also is provided with a second port and suction tube 7 to be connected to a suction regulator to provide suction within the bag so as to draw blood into the bag from the surgical site. The bottom end wall of the bag is provided with an outlet port and tube 8 to withdraw blood from the bag to be reinfused into the patient.

The autotransfusion bag is provided with releasable means for maintaining the bag in an open position. A spreader arm 9 extends across the upper end wall of the autotransfusion bag and a spreader arm 10 extends across the bottom end wall of the bag. The spreader arms are provided with downwardly extending arms 11 which extend into sockets 12 which are integrally formed along the center line adjacent the upper and lower ends of the semi-rigid side walls 3 and 4. Thus, when the spreader arms 9 and 10 engage the socket members 12 disposed on the upper and lower ends of the semi-rigid side walls 4 and 5, the sidewall shells 4 and 5 are forced into a curved configuration so as to maintain the bag in the open position as shown in FIG. 1. As seen in FIG. 1 there are provided locking pins 13 which extend through apertures in sockets 12 and engage recesses 14 in the spreader arms 9 and 10. By withdrawing the spreader arms 9 and 10 from the socket members 11, the bag is readily released to a flattened condition as shown in FIG. 2.

Figure 4:
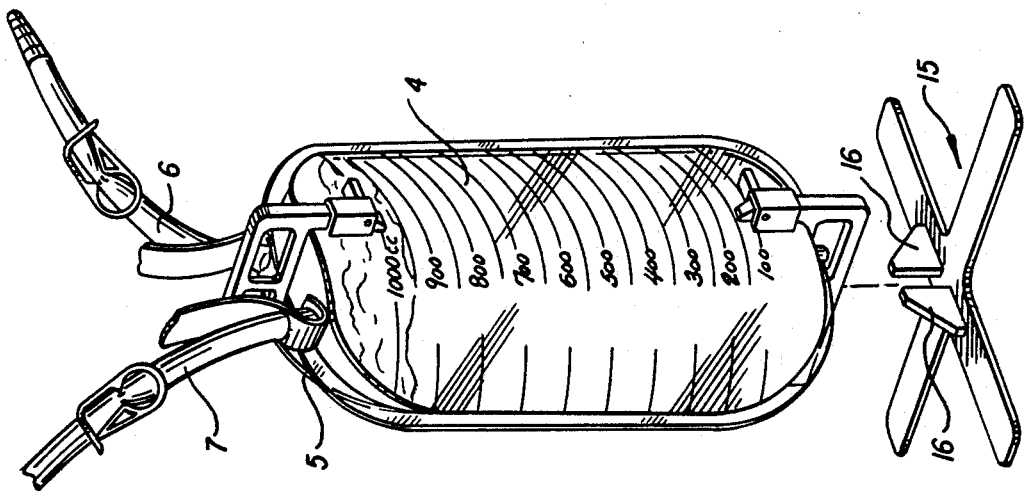
FIG. 4 is a perspective view of the bag removed from the stand.
Figure 3:
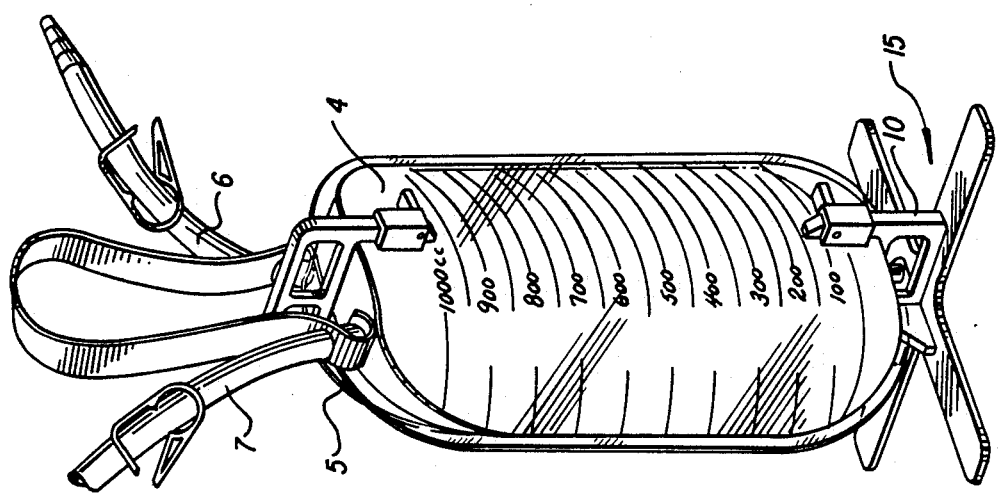
FIG. 3 is a perspective view of the bag in fully open condition supported on a stand.

As seen in FIGS. 3 and 4, a detachable floor stand 15 is provided which releasably receives the spreader arm 10 within a slot formed in upstanding retainer elements 16 mounted on the floor stand 15. Alternatively, the bag may be supported by means of a bag hanger 17 secured to the upper end of the bag engaging the tubes 5 and 6 as shown in FIG. 2.

In use, the bag 1 is extended to the open position by means of engagement of the spreader arms 9 and 10 with the semi-rigid side walls 4 and 5. The tube 7 is connected to suction and the inlet tube 6 has the open end thereof in communication with the surgical site so as to draw blood into the bag. When the bag is filled, the tubes 6 and 7 are clamped closed and the spreader arms 9 and 10 are removed from engagement with the sockets 12 on the side walls 4 and 5 of the bag. It will be noted that apertures are provided in the spreader arms for engagement with the fingers to permit ready removal of the spreader arms. With the spreader arms removed from the bag, the outlet 8 at the lower end of the bag may be connected with an IV tube to reinfuse the blood within the bag into the patient. The bag will collapse as the blood is removed from the interior of the bag.

Obviously, many modifications and variations of the present invention are possible in light of the above teachings. What is claimed as new and is desired to be secured by letters patent is:

We claim:

1. An autotransfusion bag comprising a pair of semi-rigid substantially flat side wall shells having top, bottom and side edges, a flexible bag, outer surfaces of the bag being secured to inner surfaces of said semirigid sidewall shells, said flexible bag having a width substantially equal to the width of the semirigid sidewall shells so that the side edges of the pair of sidewalls hells are maintained in closely spaced relationship and the flexible bag having a length substantially greater than the length of the semirigid sidewall shells whereby when the semirigid sidewall shells are substantially flat, end portions of the flexible bag extend beyond the top and bottom edges of the semirigid sidewalls, and means extending across at least one of said top and bottom edges of said semirigid sidewall shells for retaining said sidewall shells in an outwardly curved shape to expand said flexible bag with the end portions of the flexible bag disposed between the top and bottom edges of the semirigid sidewall shells and with the side edges of the pair of sidewall shells being in closely spaced relationship.

2. An autotransfusion bag according to claim 1 wherein said last named means comprises a support spreader having arms at each end thereof for engagement with retainer means mounted on said semirigid side walls.

3. An autotransfusion bag according to claim 2 wherein said last named means comprises support spreaders at the top and bottom ends of the bag.

4. An autotransfusion bag according to claim 1 and further including a detachable floor stand engageable with the support spreader at the bottom of the bag.

* * * * *